(12) United States Patent
Caleffi et al.

(10) Patent No.: US 8,708,943 B2
(45) Date of Patent: Apr. 29, 2014

(54) HEMO(DIA) FILTRATION APPARATUS

(75) Inventors: Luca Caleffi, Carpi (IT); Marco Paraluppi, Medolla (IT); Giuseppe Franzoni, Sassuolo (IT)

(73) Assignee: Gambro Lundia AB, Lund (SE)

( * ) Notice: Subject to any disclaimer, the term of this patent is extended or adjusted under 35 U.S.C. 154(b) by 372 days.

(21) Appl. No.: 12/447,796

(22) PCT Filed: Oct. 30, 2006

(86) PCT No.: PCT/IB2006/003029
§ 371 (c)(1),
(2), (4) Date: Jun. 8, 2010

(87) PCT Pub. No.: WO2008/053259
PCT Pub. Date: May 8, 2008

(65) Prior Publication Data
US 2010/0241044 A1 Sep. 23, 2010

(51) Int. Cl.
*A61M 37/00* (2006.01)
(52) U.S. Cl.
USPC ........................................................ 604/5.04
(58) Field of Classification Search
USPC ........................................................ 604/5.04
See application file for complete search history.

(56) References Cited

U.S. PATENT DOCUMENTS

| | | | |
|---|---|---|---|
| 4,436,620 A | 3/1984 | Bellotti et al. | |
| 4,468,329 A * | 8/1984 | Shaldon et al. | 210/651 |
| 4,666,598 A | 5/1987 | Heath et al. | |
| 4,702,829 A * | 10/1987 | Polaschegg et al. | 210/195.2 |
| 4,711,715 A * | 12/1987 | Polaschegg | 210/103 |
| 4,715,959 A * | 12/1987 | Allan et al. | 210/637 |
| 5,024,756 A * | 6/1991 | Sternby | 210/93 |
| 5,211,849 A * | 5/1993 | Kitaevich et al. | 604/5.04 |
| 5,247,434 A * | 9/1993 | Peterson et al. | 700/83 |
| 5,326,476 A * | 7/1994 | Grogan et al. | 210/646 |
| 5,344,568 A * | 9/1994 | Kitaevich et al. | 210/645 |
| 5,441,636 A | 8/1995 | Chevallet et al. | |
| 5,487,827 A * | 1/1996 | Peterson et al. | 210/87 |
| 5,662,806 A * | 9/1997 | Keshaviah et al. | 210/739 |
| 5,690,831 A * | 11/1997 | Kenley et al. | 210/646 |
| 5,702,606 A * | 12/1997 | Peter et al. | 210/646 |
| 5,725,776 A * | 3/1998 | Kenley et al. | 210/646 |
| 6,083,187 A * | 7/2000 | Nakayama et al. | 604/6.01 |
| 6,200,485 B1 * | 3/2001 | Kitaevich et al. | 210/739 |

(Continued)

FOREIGN PATENT DOCUMENTS

| | | | |
|---|---|---|---|
| IT | 1222122 A | 7/1987 | |
| IT | 1276447 A | 6/1995 | |

(Continued)

*Primary Examiner* — Susan Su
*Assistant Examiner* — Guy K Townsend
(74) *Attorney, Agent, or Firm* — Pearne & Gordon LLP

(57) ABSTRACT

An apparatus for hemo(dia)filtration comprises an extracorporeal blood circuit and a supply line of a replacement fluid to the extracorporeal blood circuit. The supply line has a bifurcation which divides a main branch (24) into a pre-dilution branch (25) and a post-dilution branch (26). A pump tube tract (29) is predisposed in the supply line for coupling with a circuit pump of the replacement fluid. An expansion chamber is predisposed in the extracorporeal blood circuit and is fluidly connected to the pre-dilution branch. The invention provides a disposable fluid circuit usable for performing a hemodiafiltration treatment with pre-dilution and post-dilution which is couplable simply, rapidly, economically and reliably to a machine for monitoring the treatment.

23 Claims, 12 Drawing Sheets

(56) References Cited

U.S. PATENT DOCUMENTS

| | | | |
|---|---|---|---|
| 6,284,131 B1* | 9/2001 | Hogard et al. | 210/143 |
| 6,287,516 B1* | 9/2001 | Matson et al. | 422/44 |
| 6,303,036 B1* | 10/2001 | Collins et al. | 210/646 |
| 6,406,631 B1* | 6/2002 | Collins et al. | 210/646 |
| 6,423,231 B1* | 7/2002 | Collins et al. | 210/646 |
| 6,582,385 B2* | 6/2003 | Burbank et al. | 604/5.04 |
| 6,736,972 B1* | 5/2004 | Matson | 210/650 |
| 6,780,322 B1* | 8/2004 | Bissler et al. | 210/637 |
| 6,821,431 B2* | 11/2004 | Collins et al. | 210/646 |
| 6,913,588 B2* | 7/2005 | Weitzel et al. | 604/6.09 |
| 7,067,060 B2* | 6/2006 | Collins et al. | 210/646 |
| 7,115,107 B2* | 10/2006 | Delnevo et al. | 604/6.15 |
| 7,264,607 B2* | 9/2007 | Caleffi | 604/6.16 |
| 7,285,105 B2* | 10/2007 | Kim et al. | 604/5.04 |
| 7,291,122 B2* | 11/2007 | Matson | 604/6.09 |
| 2001/0041892 A1* | 11/2001 | Burbank et al. | 606/46 |
| 2001/0045395 A1* | 11/2001 | Kitaevich et al. | 210/739 |
| 2001/0051106 A1* | 12/2001 | Matson et al. | 422/44 |
| 2003/0130607 A1* | 7/2003 | Delnevo et al. | 604/4.01 |
| 2003/0217972 A1* | 11/2003 | Connell et al. | 210/646 |
| 2003/0222022 A1* | 12/2003 | Connell et al. | 210/636 |
| 2004/0024342 A1* | 2/2004 | Weitzel et al. | 604/5.01 |
| 2004/0050789 A1* | 3/2004 | Ash | 210/646 |
| 2004/0069709 A1* | 4/2004 | Brugger et al. | 210/646 |
| 2004/0084372 A1* | 5/2004 | Connell et al. | 210/646 |
| 2004/0186416 A1* | 9/2004 | Caleffi | 604/6.16 |
| 2005/0020958 A1* | 1/2005 | Paolini et al. | 604/4.01 |
| 2005/0029193 A1* | 2/2005 | Matson | 210/645 |
| 2005/0040110 A1* | 2/2005 | Felding | 210/646 |
| 2005/0045548 A1* | 3/2005 | Brugger et al. | 210/252 |
| 2005/0065459 A1 | 3/2005 | Zhang et al. | |
| 2005/0082210 A1* | 4/2005 | Favre | 210/109 |
| 2005/0126961 A1* | 6/2005 | Bissler et al. | 210/87 |
| 2005/0131331 A1 | 6/2005 | Kelly et al. | |
| 2005/0131332 A1* | 6/2005 | Kelly et al. | 604/4.01 |
| 2005/0230292 A1 | 10/2005 | Beden et al. | |
| 2005/0245871 A1 | 11/2005 | Delnevo et al. | |
| 2006/0084906 A1* | 4/2006 | Burbank et al. | 604/6.16 |
| 2010/0268145 A1* | 10/2010 | Caleffi et al. | 604/5.04 |

FOREIGN PATENT DOCUMENTS

| | | |
|---|---|---|
| WO | 03/047656 A1 | 6/2003 |
| WO | 2004/004807 A1 | 1/2004 |
| WO | 2004/005717 A1 | 1/2004 |
| WO | 2004/082731 A2 | 9/2004 |
| WO | 2005/044341 A1 | 5/2005 |

* cited by examiner

HEMO(DIA) FILTRATION APPARATUS

BACKGROUND OF THE INVENTION

The present invention relates to an apparatus for hemo(dia) filtration.

Specifically, though not exclusively, the invention can be usefully applied for realising a disposable fluid circuit associable to a machine for on-line preparation of a dialysis fluid with the aim of performing a hemo(dia)filtration treatment.

As is known, a hemo(dia)filtration treatment comprises stages of creating an extracorporeal circulation of a patient's blood, of passing the extracorporeal blood internally of a hemo(dia)filter having a semipermeable membrane, of ultrafiltering a part of the plasmatic liquid contained in the extracorporeal blood through the semipermeable membrane, and of introducing a replacement fluid into the extracorporeal blood before (pre-dilution) and after (post-dilution) the hemo (dia)filter. The quantity of replacement fluid introduced is equal to the quantity of ultrafiltered plasmatic liquid, minus the desired weight loss of the patient.

In particular the present invention relates to an apparatus comprising an extracorporeal blood circuit having an arterial line (which takes the extracorporeal blood from the patient to the hemo(dia)filter) and a venous line (which returns the blood from the hemo(dia)filter to the patient), a replacement liquid supply line for the extracorporeal blood circuit, a bifurcation dividing a main line of the supply line into a predilution line connected fluidly to the arterial line and a postdilution line connected fluidly to the venous line, a tube pump tract, in the form of an open ring and predisposed in the supply line for coupling with a replacement liquid fluid circulation line, and an expansion chamber predisposed in the extracorporeal blood circuit and fluidly connected to the predilution branch and the post-dilution branch.

An apparatus made in this way is known, for example, in US 2005/0131331, which describes a medical fluid circuit unit for a hemodiafiltration treatment comprising: a fluid transport line having an inlet end predisposed for removable connection with an on-line preparation circuit of a dialysis fluid; a pump tract predisposed for coupling with a peristaltic pump for dialysis fluid circulation; an ultrafilter fluidly inserted in the transport line for the dialysis fluid ultrafiltration with the aim of making it suitable for infusion in an extracorporeal blood circuit as a replacement fluid; and a bifurcation in which the transport line divides downstream of the ultrafilter in a pre-dilution line, connected to the blood circuit upstream of a hemodiafilter, and a post-dilution line, connected to the blood circuit downstream of the hemodiafilter.

Italian patent IT 1222122 illustrates, in FIG. 3, an integrated module for hemodiafiltration constituted: by a chamber 1 for pre-pump arterial pressure monitoring in which the blood coming from the patient enters, provided with an attachment 2 for monitoring the pressure, an attachment 3 for a service line, an attachment point 4 for connecting to the patient, and an attachment point 5 to the arterial pump tube tract; by an arterial post-pump expansion chamber 6, connected to the pre-pump chamber by the pump tube, external of the module and subjected to the action of the arterial blood pump, and from which the blood is sent to the hemodiafilter, provided with an attachment point 7 for the arterial pump tube tract, an attachment 3 for a service line, an anticoagulant infusion point 8 and an attachment point 9 for connection with the dialyser; by a monitoring chamber 10 of the venous pressure, to which the purified blood from the hemodiafilter and a replacement fluid flow, the monitoring chamber 10 being provided with a filter 11, an attachment for a service line, an attachment point 12 of the connection in exit from the dialyser, an attachment point 13 for connection with the replacement fluid infusion, and an attachment point 20 for the infusion pump tube; by a control chamber 17 of the replacement fluid coming from one or more bags and connected to the venous chamber 10 by a pump tube subjected to the action of a peristaltic pump, provided with an attachment 3 for a service line, an attachment point 18 of the connection with the replacement bag solution, and an attachment point 19 for the infusion pump tube tract. The integrated module can be made of any thermoplastic material suitable for use in the biomedical field for contact with blood, either rigid or semi-rigid, for example polyvinyl chloride, polycarbonates etc.

U.S. Pat. No. 4,666,598 describes an extracorporeal blood circuit provided with: a cartridge including an arterial blood chamber and a venous blood chamber; a first arterial branch having a flexible tube with a first end designed for connection with a vascular access of a patient and with a second end to connected to an inlet of the arterial chamber; a pump tract formed by a flexible ring-shaped tube which extends from one side of the cartridge and has a first end connected to an outlet of the arterial chamber and a second end connected to a blood passage conduit internal of the cartridge; a second arterial branch having a flexible tube with a first end connected to the blood passage conduit and a second end designed for connection to an inlet of a membrane blood treatment device (dialyser); a first venous branch having a flexible tube with a first end designed for connection with the membrane blood treatment device and with a second end connected to an inlet of the venous chamber; a second venous branch having a flexible tube with a first end connected to an outlet of the venous chamber and a second end designed for connection to the vascular access of the patient. The cartridge exhibits three projections for mounting to the front panel of a dialysis machine, in which two projections are formed by two tubular extensions with parallel axes, arranged one above the other on a side of the cartridge adjacent to the arterial chamber, and a third projection arranged on the opposite side of the cartridge, adjacent to the venous chamber. The cartridge is placed in a work configuration by coupling each projection with a respective clip, arranged on the panel of the dialysis machine.

U.S. Pat. No. 5,441,636 describes an integrated blood treatment module comprising a support element in the form of a quadrilateral plate bearing on each side thereof four opening shaped pump tracts, projecting towards the outside of the periphery of the support element and designed for coupling with respective peristaltic pumps, and a device for membrane blood treatment (dialyser) fixed to the centre of the support element and having a blood chamber, fluidly connected to a pump tract for blood circulation, a fluid chamber fluidly connected to a pump tract for circulation of fresh dialysis liquid and a pump tract for circulation of exhausted dialysis liquid, and a semipermeable membrane which separates the blood chamber from the fluid chamber. The support element is mounted on a blood treatment apparatus by means of four elastic engagement fingers which extend from the front panel of the apparatus and which snap into openings afforded in the support element at opposite sides of the membrane blood treatment device.

WO 2004/004807 describes a circuit for infusion of a medical fluid in an extracorporeal blood circuit, comprising: a fluid transport line connected with a bag of medical fluid to be infused into the extracorporeal blood circuit; a flat support element having two tubular extensions to which the two ends of an open-ring pump tract are connected, the pump tract being predisposed for coupling with a peristaltic pump for circulation of the medical fluid; and a double-membrane air separator arranged fluidly downstream of the pump tract and integrated with the support element. The air separator comprises a hydrophilic membrane which holds back the gaseous component of the medical fluid and a hydrophobic membrane arranged in a breather for evacuation of the gaseous component. The support element exhibits at the centre thereof a through-opening which is used for mounting the element on a panel of a medical apparatus provided with the peristaltic pump.

Italian patent IT 1276447 describes a blood line which forms an integrated unit comprising an arterial line and a venous line connected to one another at a drip chamber belonging to the venous line. The drip chamber is formed by a container that is superiorly closed by a cap. A through-hole is afforded internally of the cap, which through-hole belongs to the arterial line and exhibits at the ends thereof connections for tracts of tube of the arterial line. One of these connections is fixed at an end of an arterial pump tract, the other end of which is fixed to a connection and support element which is fixed to the outside of the container and which is further connected fluidly to a patient tract of the arterial line.

U.S. Pat. No. 4,436,620 describes an integral hydraulic circuit for a hemodialysis apparatus which comprises a rigid and flat cartridge which defines three blood chambers constituted by a pre-pump arterial blood chamber, a post-pump arterial blood chamber, and a venous chamber. The cartridge further defines two tubular extensions for coupling the arterial pump tract which fluidly connects the pre-pump chamber with the post-pump chamber, and gripping organs for engaging a dialyser connected fluidly to the blood flow line.

WO 2005/044341 describes an integrated blood treatment module comprising a blood treatment device in the form of a hollow fibre filter provided with a tubular housing rigidly connected with two tubular extensions to which the ends of a pump tract for a peristaltic pump are coupled. The module further comprises a venous chamber for air/blood separation.

US 2005/0230292 describes a hemodialysis cartridge with an integrated dialyser, in which the cartridge comprises a rigid base body affording various recesses which are covered by an elastomer sheet. These recesses, in collaboration with the elastomer covering sheet, define blood passages, an arterial measuring chamber, and two blood pumping chambers. The cartridge is coupled to a hemodialysis machine provided with various actuators and sensors which interact with the elastomer sheet.

One of the problems in the prior art is that of providing a disposable fluid circuit which is usable for performing a hemo(dia)filtration treatment with pre-dilution and/or post-dilution and which is couplable simply, rapidly, economically and reliably to a machine for monitoring the treatment.

SUMMARY OF THE INVENTION

An aim of the present invention is to obviate the above-mentioned drawback in the prior art.

A further aim of the invention is to provide an apparatus which enables hemo(dia)filtration to be performed both in pre-dilution and in post-dilution.

An advantage of the invention is that it provides a disposable apparatus for hemo(dia) filtration which is couplable simply and rapidly to a deformed-tube type pump for circulation of the replacement fluid.

A further advantage is to make available an apparatus which is operatively associable, and easily so, to a device predisposed on the treatment monitoring machine in order to monitor the replacement fluid pressure.

A still further advantage is that it gives rise to a small-volume apparatus which is easy to handle.

These and other aims besides are all attained by the object as it is characterised in the appended claims.

Further characteristics and advantages of the present invention will better emerge from the detailed description that follows, of at least an embodiment of the invention, illustrated by way of non-limiting example in the figures of the accompanying drawings.

BRIEF DESCRIPTION OF THE DRAWINGS

The description will be made herein below with reference to the appended figures of the drawings, provided by way of non-limiting example, in which.

DETAILED DESCRIPTION

Figure 1:
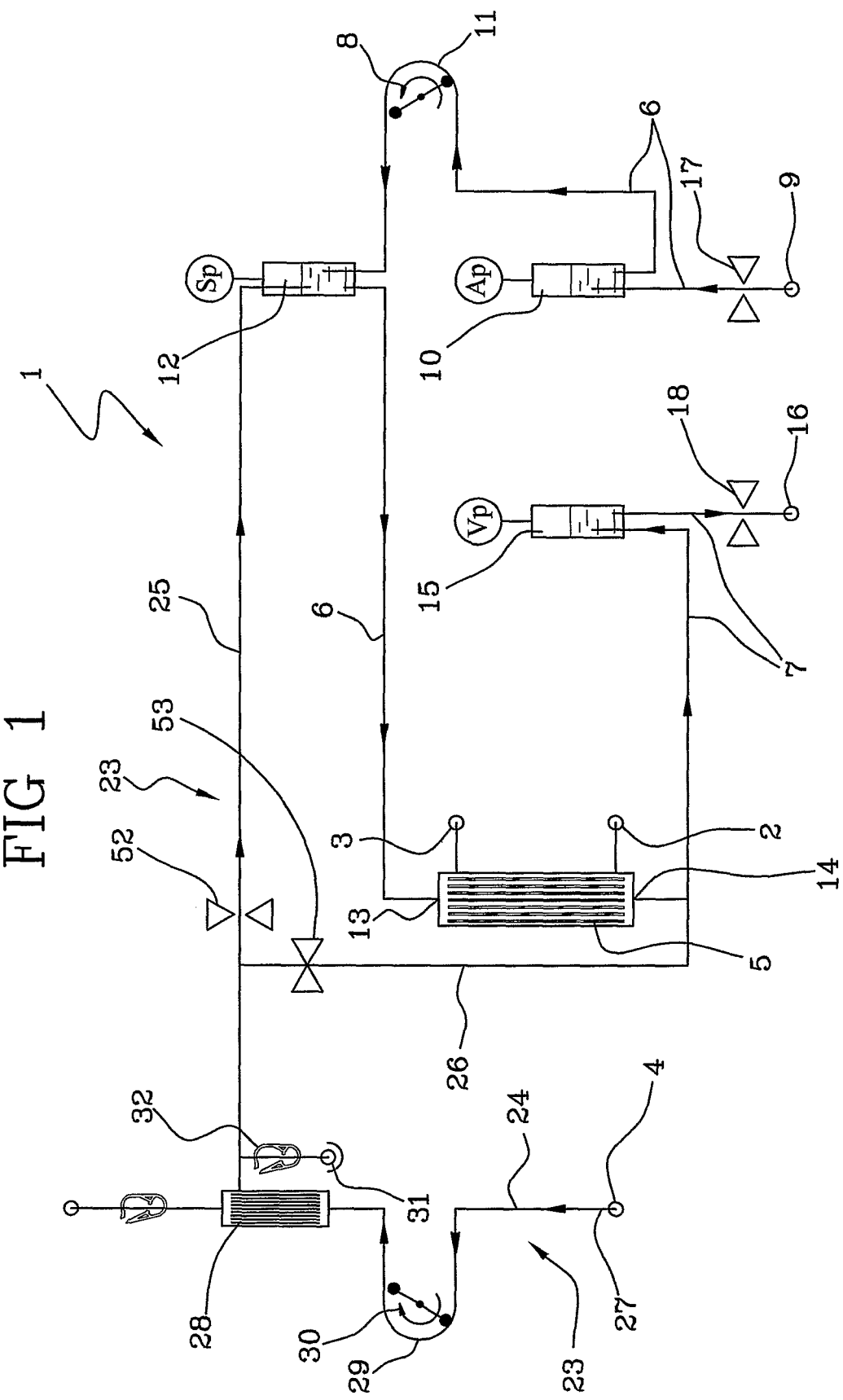
FIG. 1 is a diagram of the hemo(dia)filtration apparatus of the invention.
Figure 2:
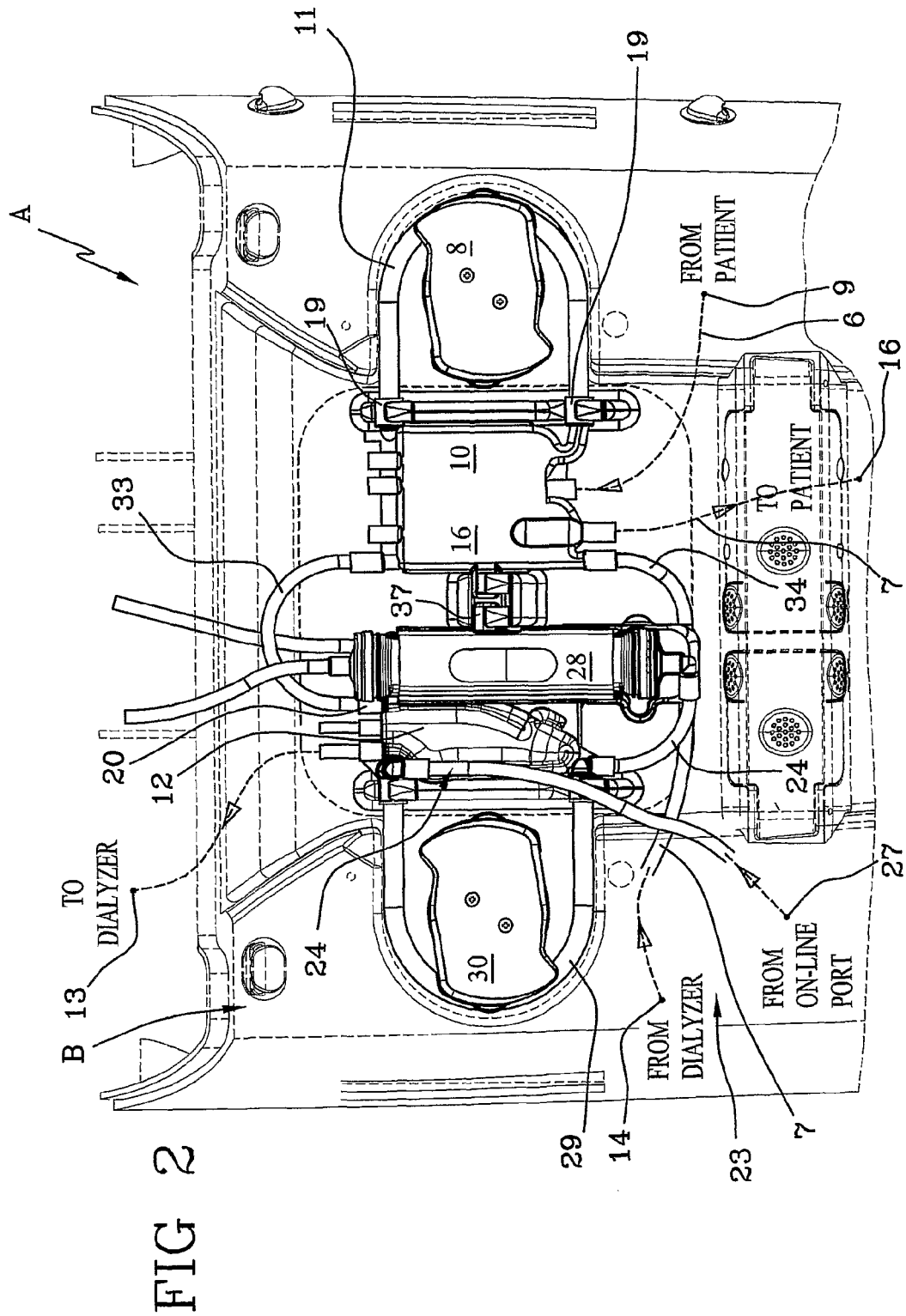
FIG. 2 is a front view of an apparatus made according to the diagram of FIG. 1, and applied operatively to the front panel of a machine for dialysis.
Figure 3:
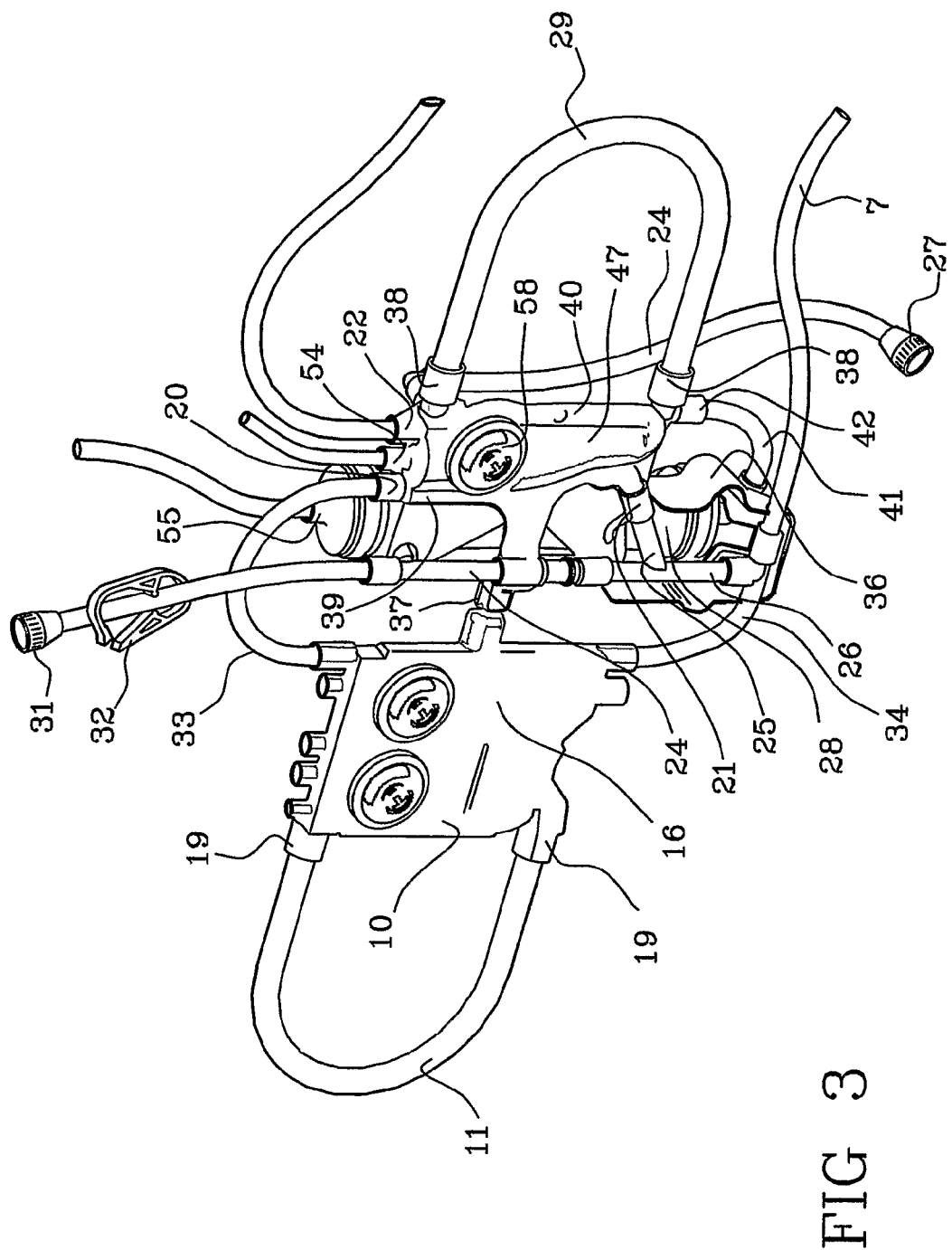
FIG. 3 is a perspective view from behind of the apparatus of FIG. 2, with some parts removed better to evidence others.
Figure 4:
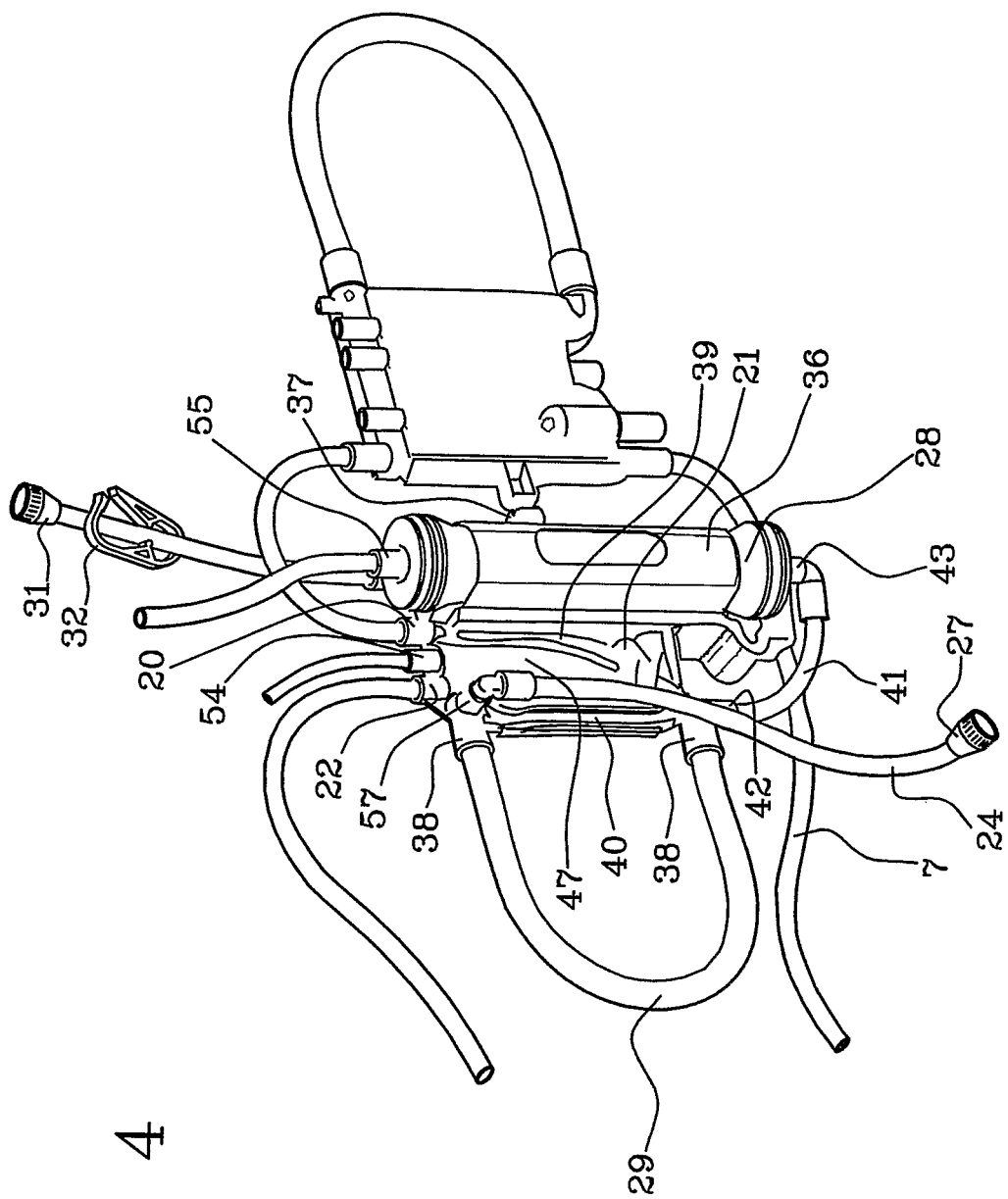
FIG. 4 is a perspective view from the front of FIG. 3.

With reference to FIG. 1, 1 denotes in its entirety an extracorporeal blood treatment apparatus destined for coupling to a machine for extracorporeal blood treatment able to provide a treatment fluid. In the following description the extracorporeal blood treatment apparatus will be called a hemo(dia) filtration apparatus 1, the extracorporeal blood treatment machine will be called a dialysis machine and the treatment fluid will be called dialysis fluid, without any more generalised references being lost by use of this terminology. In particular the dialysis machine produces on-line a dialysis fluid of predetermined chemical composition (for example by mixing water and solid and/or liquid concentrates). The dialysis machine is able to reduce the concentration of endotoxins in the dialysis fluid (for example by passage of dialysis fluid through one or more stages of ultrafiltration). The dialysis machine is able to provide a control system of patient weight loss during the treatment (for example by a control of the difference between the dialysis fluid delivery at the inlet and outlet of the blood treatment device thanks to the use of two pumps arranged before and after the blood treatment device—hereinafter hemo(dia)filter—and of two flowmeters arranged before and after the hemo(dia)filter). The hemo(dia)filtration apparatus 1 can be composed, all or in part, by disposable elements. The dialysis machine (of which the front panel is partially illustrated in FIG. 2) is of known type, is provided with a fresh dialyser fluid port 2 (see the diagram of FIG. 1), from which the dialysis fluid to be introduced in the hemo(dia) filter is taken, an exhausted fluid port 3, in which the fluid exiting the hemo(dia)filter is discharged (made up of used dialysis fluid and/or of ultrafiltrate), and an on-line port 4 from which the dialysis fluid, to be processed for use as replacement fluid in hemo(dia)filtration treatment, is taken. The dialysis machine is further provided with a system of known type and not illustrated, for preparation of the dialysis fluid; this system is connected to a main dialysis fluid supply line, which terminates in the fresh dialysate port 2. A secondary dialysis fluid supply line, which branches from the main supply line, terminates in the on-line port 4. The dialysis machine is further provided with an exhausted liquid discharge line which originates at one end at the exhausted liquid port 3 and which terminates at the other end thereof in a drainage (of known type and not illustrated). When the hemo(dia)filtration apparatus 1 is used as a hemofiltration apparatus 1, the fresh dialysate port 2 is closed, or non-operative, or, in a further embodiment, absent.

The hemo(dia)filtration apparatus 1 comprises the hemo (dia)filter 5 having a blood chamber and a fluid chamber (not illustrated) which are separated from one another by a semipermeable membrane (not illustrated) which, in this case, comprises a bundle of hollow fibres. In this embodiment the blood chamber comprises the space internally of the hollow fibres, while the fluid chamber comprises the space externally of the hollow fibres. The fluid chamber is further at least partially defined by the tubular body containing the bundle of hollow fibres. The hemo(dia)filtration apparatus 1 comprises an extracorporeal blood circuit having an arterial line 6, or a blood removal line from the patient for the blood to be treated in the hemo(dia)filter 5, and a venous line 7, or patient return line for the blood treated in the hemo(dia)filter 5. The hemo (dia)filtration apparatus 1 further comprises a blood pump 8 for circulation of blood in the extracorporeal circuit. The blood pump 8 is of a tube-deforming rotary type (peristaltic). The extracorporeal blood circuit further comprises the blood chamber of the hemo(dia)filter 5. The arterial line 6 comprises an arterial patient end 9, a pre-pump arterial expansion chamber 10, a blood pump tube tract 11, a post-pump arterial expansion chamber 12, an arterial device end 13. The venous line 7 comprises a venous device end 14, a venous expansion chamber 15, a venous patient end 16. The dialysis machine is provided with an arterial clamp 17 operating on the arterial line 6, in particular between the patient arterial end 9 and the pre-pump arterial expansion chamber 10. The dialysis machine is provided with a venous clamp 18 operating on the venous line 7, in particular between the patient venous end 16 and the venous expansion chamber 15. The patient arterial end 9, like the patient venous end 16, is designed for connection (directly or via a vascular access device of known type) with a vascular access of a patient. The arterial clamp 17, respectively the venous clamp 18, serves for closing a squeezable tract of the arterial line 6, respectively of the venous line 7, on command of a control unit of the dialysis machine. The pre-pump arterial expansion chamber 10, which is arranged downstream of the arterial clamp 17 (where "downstream" means with reference to the blood circulation direction during the treatment), serves for separating the air contained in the blood and for monitoring the arterial blood pressure (before the blood pump 8). The venous expansion chamber 15, which is arranged upstream of the venous clamp 18 (where "upstream" means with reference to the blood circulation direction during the treatment), is for separating the air contained in the blood and for monitoring the venous blood pressure. The pre-pump arterial expansion chamber 10, like the venous expansion chamber 15, is designed to give rise to a liquid level separating a lower part full of liquid (blood) from an upper part full of gas (air). Each of the expansion chambers 10 and 15 is provided, for example superiorly, with a zone predisposed for pressure reading; this zone comprises, in the specific case, a membrane device, of known type, having a deformable elastic membrane with an internal surface in contact with the fluid (blood and/or air) contained in the chamber and an external surface operatively associable to a pressure sensor of the dialysis machine. The blood pump tube tract 11, which is designed for removably coupling with the blood pump 8, is open-ring conformed (in the specific embodiment it is U-shaped with a horizontal lie and with the convexity facing right, with reference to the viewpoint of a user situated in front of the front panel of the dialysis machine) with two ends, one for blood inlet and the other for blood outlet, fluidly and mechanically connected to two tubular extensions 19 (FIG. 2) solidly connected to the pre-pump arterial expansion chamber 10. The arterial device end 13 and the venous device end 14 are designed for removably coupling with an inlet port (in the specific embodiment, upper) and, respectively, an outlet port (in the specific embodiment, lower) of the blood chamber of the hemo(dia)filter 5. The pre-pump arterial expansion chamber 10 and the venous expansion chamber 15 are integrated in a cartridge structure of known type.

The post-pump arterial expansion chamber 12 is inserted in the arterial line 6 between the blood pump 8 and the hemo (dia)filter 5. The post-pump arterial expansion chamber 12 comprises a blood inlet port 20, an infusion fluid inlet port 21 (in the present example of hemo(dia)filtration with pre-dilution, the infusion fluid, or infusate, can be replacement fluid, or substitute; in the following description the specific term "replacement fluid" and "substituate" will be used instead of more general terms like "infusion fluid" and "infusate", without the generalised meaning being compromised), a mixing zone where the blood and replacement fluid are mixed, and an outlet port for the blood-fluid mixture 22 (where the replacement fluid is present in the mixture in case of pre-dilution and absent in case of no pre-dilution).

The post-pump arterial expansion chamber 12 serves to separate the air contained in the replacement fluid. The post-pump arterial expansion chamber 12 monitors the pressure in the replacement fluid supply line. The post-pump arterial expansion chamber 12 also serves to further separate the air contained in the blood along the arterial line 6 downstream of the blood pump 8 and for monitoring the blood pressure in the arterial line 6 between the blood pump and the hemo(dia)filter 5. The post-pump arterial expansion chamber 12 is designed to produce a liquid level that separates a lower part which is full of liquid (blood or blood/replacement fluid mixture) and an upper part which is full of gas (air). The post-pump arterial expansion chamber 12 is provided, for example superiorly, with a zone predisposed for pressure detection; this zone comprises, in the present embodiment, a membrane device 58, of known type, having a deformable membrane with an internal surface in contact with the fluid contained in the chamber and an external surface which is operatively associable to a pressure sensor of the dialysis machine. The post-pump arterial expansion chamber 12 will be described in greater detail herein below.

The hemo(dia)filtration apparatus 1 comprises a replacement fluid supply line 23 which provides, in this embodiment, the replacement fluid (substituate) to the extracorporeal blood circuit. The supply line 23 takes the dialysis fluid from the on-line port 4 and, after an ultrafiltration treatment to make it suitable as a replacement fluid, conveys it to the extracorporeal blood circuit.

The supply line 23 branches out from a main branch 24 into a pre-dilution branch 25 fluidly connected to the arterial line 6 and a post-dilution branch 26 fluidly connected to the venous line 7. The replacement fluid supply line 23 comprises an inlet end 27 having a connector for removable connection with the on-line port 4 for sourcing the dialysis fluid supplied by the dialysis machine. Alternatively to an on-line port of a machine for dialysis fluid preparation, other fluid sources can be used, for example a ready-prepared dialysis fluid or replacement fluid recipient, or a centralised dialysis fluid supply system, supplying to various units.

The replacement fluid supply line 23 comprises an ultrafilter 28 predisposed fluidly in the main branch 24 upstream of the branch-out for ultrafiltering the dialysis fluid taken from the dialysis machine to render the fluid suitable for use as a replacement fluid. The ultrafilter 28 reduces the endotoxin percentage in the fluid. The ultrafilter 28 comprises a semipermeable membrane that separates a first chamber containing the fluid to be ultrafiltered (dialysis fluid) from a second chamber containing the ultrafiltered fluid (replacement fluid). The semipermeable membrane comprises, in the present embodiment, a bundle of hollow fibres. The first chamber of the fluid to be ultrafiltered comprises the inside of the hollow fibres, while the second chamber of the ultrafiltered fluid is defined between the outside of the hollow fibres and the tubular body enclosing the bundle of hollow fibres.

The ultrafilter 28 is further provided, for example superiorly, with a vent line of the air communicating with the first chamber of the fluid to be ultrafiltered and having a clamp (for example manually activated) for intercepting and a vent into the atmosphere protected by a protection device (for example a hydrophobic membrane).

The replacement fluid supply line 23 can further comprise a check valve predisposed fluidly in the main branch 24 upstream of the branch-out. The check valve, which in the present embodiment is not present, might be located after the ultrafilter 28.

A tract of the replacement fluid pump tube 29 is predisposed in the supply line 23 for coupling with a replacement fluid circulation pump 30. In the present embodiment the replacement fluid pump 30 is a tube-deforming rotary pump (peristaltic). The replacement fluid pump tube tract 29 is open-ring shaped with an aspiration end and a delivery end. In particular the replacement fluid pump tube tract 29 is U-shaped, and, in the use configuration with the pump 30, lies on a vertical plane, with the two end branches arranged horizontally (the convexity of the U is directed oppositely to the blood pump tube tract 11, i.e. in the present embodiment to the left with reference to the viewpoint of a user situated in front of the front panel of the machine). The rotation axes of the two rotary pumps 8 and 30 are parallel to one another. The pump tube tract 29, in the engaged configuration with the pump 30, is arranged symmetrically to the blood pump tube tract 11, with respect to a plane of symmetry (in the present embodiment, vertical) which is parallel to the rotation axes of the two rotary pumps 8 and 30. The replacement fluid pump tube tract 29 is fluidly arranged in the main branch 24 upstream of the branch-out (where "upstream" means in reference to the circulation direction of the replacement fluid). The replacement fluid pump tube tract 29 is arranged fluidly upstream of the ultrafilter 28.

The replacement fluid supply line 23 comprises an auxiliary connection 31 fluidly arranged after the ultrafilter 28. This auxiliary connection 31 is branched out from the replacement fluid line 23. The auxiliary line is further provided with a clamp 32 (for example a manually operated clamp) for closing the auxiliary line, and a protection hood for removable closure of the auxiliary line 31. The auxiliary line branches off from the main branch 24 before the branch-out.

The auxiliary connection 31 is designed for removable fluid connection with the extracorporeal blood circuit, in particular with the arterial line 6 or the venous line 7. The auxiliary connection 31 serves to fill the extracorporeal circuit with the replacement fluid, in particular during the circuit priming stage, i.e. during the stage preliminary to the treatment during which the air and any other undesirable particles contained in the blood circuit are evacuated and the circuit is filled with an isotonic liquid, for example a saline solution coming from a bag or, as in the present embodiment, with an isotonic fluid (dialysis fluid or saline) which is prepared by the dialysis machine, supplied to the on-line port 4 of the machine and ultrafiltered by crossing the replacement fluid supply line 23. In the present embodiment the auxiliary connection 31 is removably couplable to the patient end of the arterial line 9 or to the patient end of the venous line 16. The auxiliary connection 31 comprises, for example, a female luer connector couplable to a male luer connector at the patient arterial 9 or venous 16 end.

At least one from among the three above-mentioned expansion chambers (arterial pre-pump 10, arterial post-pump 12 and venous 15) is fluidly connected, in particular directly, to the pre-dilution branch 25 or the post-dilution branch 26. In the present embodiment the post-pump arterial expansion chamber 12 is fluidly connected directly to the pre-dilution branch 25.

The post-dilution branch 26 opens (directly) into a point of venous line 7 comprised between the hemo(dia)filter 5 and the venous chamber 15. The venous chamber 15 therefore indirectly communicates, via a tract of venous line 7, with the post-dilution branch 26.

The aspiration and delivery ends of the replacement fluid pump tube tract 29 are rigidly connected to at least one from among the above-mentioned expansion chambers (arterial pre-pump 10, arterial post-pump 12 and venous 15). In the present embodiment the aspiration and delivery ends of the replacement fluid pump tube tract 29 are connected rigidly to the post-pump arterial expansion chamber 12. As mentioned, the expansion chamber bearing the replacement fluid pump tube tract 29, i.e. the chamber 12, is provided with a zone for monitoring the pressure which is predisposed for connection with a pressure sensor provided on the dialysis machine. This monitoring zone is provided with the pressure detecting device 58.

Two tubular extensions for fluid and mechanical connection of the two ends of the pump tube tract 29 are solidly connected (for example are made in a single piece with the chamber itself) to the chamber 12. The two tubular extensions are not fluidly connected to the chamber 12, if not indirectly through other parts (for example the ultrafilter 28) of the fluid circuit transporting the replacement fluid.

The replacement fluid supply line 23 comprises a fluid communication system which is interpositioned fluidly between the delivery end of the replacement fluid pump tube tract 29 and the expansion chamber bearing the replacement fluid pump tube tract 29 (as mentioned in this case the expansion chamber bearing the pump tube tract 29 is the post-pump arterial expansion chamber 12). This fluid communication system comprises one or more from the following elements: the ultrafilter 28, the check valve (if present), the branch-out, and at least a tube tract which is flexible and closable by elastic deformation, in particular squeezing.

In the present embodiment, the fluid communication system, which places the replacement fluid pump tube tract 29 in communication with the extracorporeal blood circuit, comprises a first flexible tube 41 having a first end connected with a first tubular connection 42 which is rigidly connected to (but not fluidly communicating with) the post-pump arterial chamber 12 (the first tubular connection 42 is arranged inferiorly of the chamber 12 itself), and a second end which is opposite the first end and connected to a second tubular connection 43 for inlet of the ultrafilter 28 (the second tubular connection 43 for inlet is located inferiorly of the ultrafilter 28 and communicates with the chamber of the fluid to be ultrafiltered). Each of these tubular connections 42 and 43 faces downwards, with reference to an operative configuration of the apparatus 1. Each of these tubular connections 42 and 43 has a longitudinal axis which extends, at least prevalently, in a vertical direction.

The above-described fluid communication system comprises the ultrafilter 28 and a second three-way flexible tube 44 having a first end which is connected to a tubular connection for for outlet of the ultrafilter 28 (the tubular outlet connection is located on a side of the ultrafilter 28 itself, in particular superiorly, and communicates with the ultrafiltrate fluid chamber, i.e. with the outside of the hollow fibres), a second end (arranged superiorly and facing upwards) to which the auxiliary connection 31 is connected by means of the auxiliary line, and a third end (arranged inferiorly and facing downwards).

The above-mentioned three ends of the second flexible tube 44 are in reciprocal fluid communication (for example with reciprocal T or Y arrangement). The second three-way flexible tube 44, which in the present embodiment is T-shaped with the first end arranged at 90° to the other two, is press-formed by injection of a soft plastic material.

The fluid communication system comprises a third three-way flexible tube 45 having a first end which is connected to the third end of the second flexible tube 44, a second end connected to the inlet port 21 of the replacement fluid to the chamber 12, and a third end connected to a zone of the venous line 7 arranged upstream of the venous expansion chamber 15. In the present embodiment the first end is arranged superiorly (facing upwards), the third end is arranged inferiorly (facing downwards), while the second end is arranged obliquely (facing upwards) with respect to the other two, forming an angle which is less than a right-angle with the first upper end. The third three-way flexible tube 45 is made by press-forming by injection of a soft plastic material. The third three-way flexible tube 45 exhibits the branch-out in the pre-dilution branches 25 and the post-dilution branches 26, which comprise two of the three ways of the third flexible tube 45 (in particular the ways that exhibit the second and third ends).

The hemodiafiltration apparatus 1 is made in two distinct modules which are fluidly connected one to the other. A first module A (on the right in FIG. 2) comprises an initial tract of arterial line 6 which goes from the patient arterial end 9 to the pre-pump expansion chamber 10. The first module A further comprises the pre-pump expansion chamber 10, the blood pump tube tract 11 and the venous expansion chamber 15 (integrated with the chamber 10 in the cartridge structure of known type). The first module A further comprises a final tract of venous line 7 which goes from the venous expansion chamber 15 to the patient venous end 16. The first module A also comprises a tract of arterial line 6 which is arranged downstream of the blood pump 8 and which is integrated into the cartridge body structure. As mentioned, the cartridge structure, which incorporates the chambers 10 and 15, supports the two ends, aspiration and delivery, of the blood pump tube tract 11.

A second module B (on the left in FIG. 2) comprises the replacement fluid supply line 23 (starting from the inlet end 27, and including the replacement fluid pump tube tract 29, the ultrafilter 28 and the pre-dilution and post-dilution branches 25 and 26). The second module B further comprises the post-pump arterial expansion chamber 12. Also included are an intermediate tract of arterial line 33 which fluidly connects an arterial outlet of the first module A (connected to an outlet of the blood pump tube tract) with an arterial inlet of the second module B (connected to the blood inlet of the post-pump arterial expansion chamber), and an intermediate tract of venous line 34 which fluidly connects a venous outlet of the second module B (connected with the post-dilution branch 26) with a venous inlet of the first module A (connected with an inlet of the venous expansion chamber).

The second module B comprises a support element to which the supply line of the replacement fluid 23 is constrained in order that the pre-dilution 25 and post-dilution branches 25 and 26 are positioned in a prefixed position with respect to the post-pump arterial expansion chamber. The correct and stable positioning of the pre-dilution and post-dilution branches 25 and 26 with respect to the front panel of the dialysis machine enables operatively efficient use of the above-said branches with two control valves, a pre-dilution control valve 52 and a post-dilution control valve 53 arranged on the front panel.

The support element comprises, in the present embodiment, one or more extensions 35 which emerge from the expansion chamber which bears the replacement fluid pump tube tract 29 (i.e. the post-pump arterial chamber 12). The extensions 35 emerge from a side of the chamber 12 located on the opposite side with respect to the replacement fluid pump tube tract 29 and extend in an opposite direction with respect to the extension of the pump tract 29 itself. The extensions 35, in the present embodiment, are rigidly connected to the chamber 12 that bears the replacement fluid pump tube tract 29. The extensions 35, in the present embodiment, are made (for example by press-forming of plastic material) in a single piece with the chamber 12 itself. The support element further comprises a casing 36 engaged to one or more of the extensions 35. The casing 36 in the present embodiment is joint-coupled to one or more of the extensions 35. In particular the casing 36 is coupled to one or more of the extensions 35 in at least two joint zones. The casing 36, made of plastic material, is provided with a front part which at least partially contains the tubular body of the ultrafilter 28.

One of the extensions 35 exhibits a mounting extension 37 which, in collaboration with the two tubular extensions 38 for engagement of the ends of the replacement fluid pump tube tract 29, serve for removably mounting the second module B on the front panel of the dialysis machine.

The pre-dilution 25 and post-dilution 26 branches each comprise at least a tract of flexible tube which can be obstructed by squeezing. These tracts of flexible tube are positioned in a prefixed position with respect to the post-pump arterial expansion chamber 12. The correct positioning of the prefixed position is easily reached when mounting the module B on the front panel of the machine, by virtue of the fact that the fluid connection system formed by the second flexible tube 44 and the third flexible tube 45 are positioned stably with respect to the support element of module B, so that the pre-dilution 25 and post-dilution 26 branches (made from the third flexible tube 45) are immobile with respect to the support element of module B, although each of them is elastically deformable and therefore closable by squeezing of the valves 52 and 53.

The branch from the pre-dilution 25 and post-dilution 26 branches which is not fluidly connected to the espansion chamber bearing the replacement fluid pump tube tract 29 can be constrained, directly or via a tract of the extracorporeal blood circuit, to the support element. In the present embodiment, in which the expansion chamber bearing the replacement fluid pump tube tract 29 is the post-pump expansion chamber 12 (which chamber 12 is connected to the pre-dilution branch 25), the post-dilution branch 26 can be constrained to the support element via a tract of venous line 7 of the extracorporeal blood circuit. In particular, a tract of venous line 7 is engaged in two recesses afforded in the casing 36, and the post-dilution branch 26 is fluidly connected to this tract of venous line 7.

The main branch 24 of the supply line 23 is constrained (for example directly, as in the present embodiment) to the support element. In particular the main branch 24 exhibits at least a support zone that interacts (in a gripping and/or direct contact coupling) with the support element in a tract that is downstream of the ultrafilter 28. In more detail, a tract of the main branch 24 arranged downstream of the ultrafilter 28 is engaged (by, for example, a removable joint) in a seating afforded on one of the extensions 35. This tract of the main branch 24 (which in the present embodiment is part of the second flexible tube 44) exhibits, at the ends thereof, two annular projections which are axially distanced from one another and which are arranged externally of the opposite ends of the seating 46, functioning as stable centring and positioning tabs of the tract of main branch 24 in the seating 46.

The ultrafilter 28 is supportedly constrained to the support element of module B, in particular to the casing 36.

The support element can realise at least a mechanical and not fluid interconnection between the expansion chamber bearing the replacement fluid pump tube tract 29 (i.e. the chamber 12) and the replacement fluid supply line 23 and/or between the expansion chamber bearing the replacement fluid pump tube tract 29 (chamber 12) and the extracorporeal blood circuit. A mechanical and not fluid interconnection can also be operating between the expansion chamber 12 and the venous line 7 (or the post-dilution branch 26 or, respectively, the arterial line 6 (or the pre-dilution branch 25).

One of these mechanical and not fluid interconnections comprises, in the present embodiment, one of the extensions 35 in the form of an arm that emerges (on the opposite side with respect to the replacement fluid pump tube tract 29) from the expansion chamber 12 which bears the replacement fluid pump tube tract. As already mentioned, this arm exhibits at an end thereof an attachment point (seating 46) for the main branch 24 of the supply line 23. As already mentioned, the support element realises both the mechanical and not fluid interconnection between the chamber 12 and the line 23, and the mechanical and not fluid interconnection between the chamber 12 and the blood circuit.

The support element of the second module B comprises, in the present embodiment, two elements which are assembled one to the other, i.e. the extensions 35 (integrated with the chamber 12) and the protection casing 36. However it would be possible, in further embodiments of the invention, to have the support element made in an integrated single piece or an assembly of three or more distinct elements.

The second module B comprises an integrated element which defines the expansion chamber supporting the replacement fluid pump tube tract 29, i.e. the chamber 12. This integrated element also defines a part of the support element of the second module B, in particular the extensions 35.

The integrated element further defines a first conduit 39 for blood inlet into the expansion chamber 12, a second conduit 50 for replacement fluid inlet, and a third conduit 40 for blood outlet (or blood mixed with replacement fluid) from the expansion chamber 12.

The first and third blood conduit 39 and 40 belong to the extracorporeal blood circuit and are located on two opposite sides of the above-described expansion chamber 12 and extend in length in a vertical direction, with reference to an operative configuration in which the pump tube tract 29 is coupled to the replacement fluid circulation pump 30.

The first and third blood conduits 39, 40 also each have a bottom end which is fluidly connected to an expansion reservoir 47 of the post-pump arterial expansion chamber 12, and an upper end which is fluidly connected (via the ports 20 and 22) to the rest of the arterial line 6, respectively before and after the post-pump arterial expansion chamber 12. In particular the first inlet conduit 39 is connected to an initial part of the arterial blood line 6 having the patient end 9 destined for connection with the arterial vascular access; the third outlet conduit 40 is connected to a final part of the arterial blood line 6 having the device end 13 destined for connection to the hemo(dia)filter 5.

With reference to figures from 7 to 14, the integrated element defining the chamber 12 is described in greater detail. The chamber 12 comprises the expansion reservoir 47 which is provided with a bottom, a top, at least a first side extending between the bottom and the top, a first access 48 arranged on the first side at a distance from the bottom and top, and a second access 49.

The first conduit 39 terminates in the first access 48. A second conduit 50 terminates in the first conduit 39 or, as in the present embodiment, in the expansion reservoir 47. The first conduit 39 and the second conduit 50 terminate in the first access 48 with, respectively, a first flow direction and a second flow direction which are incident to one another.

The first conduit 39 terminates in the first access 48 with a first flow direction having at least a motion component directed towards the bottom. The first flow direction has at least a motion component directed towards a second side of the expansion reservoir 47; the second side extends between the bottom and top and is opposite the first side.

The second conduit 50 terminates in the expansion reservoir 47 with a second flow direction having at least a motion component directed towards the second side of the expansion reservoir 47. The second flow direction has at least a motion component directed towards the top. The second flow direction has at least a first motion component that is horizontal and directed towards the inside of the expansion reservoir 47.

The second conduit 50 comprises an intermediate tract 59 having a flow direction provided with at least a second horizontal motion component going in an opposite direction to the first horizontal motion component. The flow direction of the intermediate tract 59 is provided with at least a vertical motion component.

The first conduit 39 has a diverging tract 51 with a fluid passage that broadens in the direction of the first access 48. The diverging tract 51 broadens towards the bottom of the reservoir 47. The expansion reservoir 47 extends prevalently on a lie plane; the diverging tract 51 enlarges prevalently in a perpendicular direction to the lie plane. The diverging tract 51 terminates at the first access 48.

The first access 48 is elongate and extends in a perpendicular direction to the first side of the reservoir 47.

The second access 49 is arranged on the bottom of the reservoir 47. The third conduit 40 terminates in the second access 49. The third conduit 40 extends in length by the side of the second side of the expansion reservoir 47.

The first conduit 39 terminates in the first access 48 with a first flow direction directed towards the second access 49. The first flow direction has at least a motion component which is direction towards the bottom.

The second conduit 50 terminates on the first side of the expansion reservoir 47 below the end of the first conduit 39. The second conduit 50 terminates either in the first access 48 contiguously below the end of the first conduit 39 (as in the present embodiment), or, in a further embodiment, not illustrated, it terminates in an intermediate access arranged between the first access 48 and the bottom of the reservoir 47.

The expansion reservoir 47 has an upper part, comprised between the first access 48 and the top, having a greater width than a lower part comprised between the bottom and the first access 48.

The first conduit 39 meets the second conduit 50 in a connecting zone, and joins the connecting zone in a position above the second conduit 50.

The first conduit 39 extends lengthwise by the side of the first side of the reservoir 47. The first conduit 39 is designed to introduce the transported flow (in the present embodiment the arterial blood) into the connecting zone with at least one motion component directed in a downwards direction. The second conduit 50 is designed to introduce the transported flow (in this case the replacement fluid) into the connecting zone with at least a motion component directed upwards. The first conduit 39 and the second conduit 50 are designed so that each of the respective transported flows is introduced into the connecting zone with at least a horizontal motion component directed internally of the expansion reservoir 47.

The first conduit 39 and the second conduit 50 are arranged on a same side (the first side) of the expansion reservoir 47. The first conduit 39 is situated above the second conduit 50.

The first side of the expansion reservoir 47 has an upper zone with a vertical inclination, and a lower zone with an oblique inclination. The oblique lower zone of the first side is inclined in a direction nearing the second side. This oblique inclination determines a narrowing of the expansion reservoir 47. The zone of the second side that is facing the oblique zone of the first side is substantially vertically oriented. The first conduit 39 has an upper tract having a substantially vertical longitudinal axis, and a lower tract having an oblique longitudinal axis. The oblique axis is inclined in a direction nearing the second side of the expansion reservoir 47. The first conduit 39 terminates in the expansion reservoir 47 with an oblique inclination.

The first conduit 39 is made in a single piece with the expansion reservoir 47. The second conduit 50 is made in a single piece with the expansion reservoir 47. The third conduit 40 is made in a single piece with the expansion reservoir 47. The chamber 12 is realised by assembly of two half-shells. The two half-shells are obtained by press-forming of a plastic material.

The extracorporeal blood line which includes the chamber 12 is, in the present embodiment, the arterial line 6. The chamber 12 can, however, be associated (alternatively or in addition to the arterial line 6) to the venous line 7. The chamber 12 in this case would be a mixing chamber for replacement fluid (in post-dilution) for degassing and for monitoring pressure, arranged downstream of the hemo(dia)filter; the inlet port 20 would be connected to the hemo(dia) filter 5, while the outlet port 22 would be connected to the vascular access.

During treatment, in which the arterial line 6 and the venous line 7 are connected to the patient, the blood pump 8 is activated, so that the blood is removed from the patient via the arterial line 6, is sent to the hemo(dia)filter 5, and is returned to the patient via the venous line 7. The replacement fluid pump 30 is also activated, so that the dialysis fluid is removed from the on-line port 4 of the machine, is made to pass first through the pump tube tract 29 and then the ultrafilter 28, and is then sent selectively to the chamber 12 on the arterial line 6 (opening the pre-dilution valve 52 operating on the branch 25 and closing the post-dilution valve 53 operating on the branch 26) or to the venous line 7 (valve 52 closed and valve 53 open), or to both (valves 52 and 53 both open).

In a case of pre-dilution, the replacement fluid flow enters the expansion reservoir 47 from below, transversally encountering the blood flow that enters the reservoir from above. Both flows are obliquely directed, each with an inlet component into the expansion reservoir 47 which is horizontally directed (with reference to the work position of the chamber 12) towards the second side of the expansion reservoir 47, and a vertical component having an opposite direction to the direction of the flow. The meeting of the two flows causes an effective remixing between the blood and the replacement fluid, so that the mixed liquid (blood and replacement fluid) that exits through the third conduit 40 is homogeneously mixed.

The special conformation and arrangement of the chamber 12 enables both an effective remixing of the blood and replacement fluid and an effective degassing of the liquids entering the expansion reservoir 47, especially the replacement fluid, thus preventing any air bubbles exiting through the third conduit 40.

In the absence of pre-dilution (valve 52 closed), the replacement fluid does not reach the chamber 12, while the blood enters through the first conduit 39 and exits through the third conduit 40; since the first conduit 39 terminates directly facing the inlet of the third conduit 40, the turbulence created is relatively low, reducing to a minimum the formation of foam and flow resistors, while at the same time enabling separation of the air which may still be present in the blood.

Before the treatment is performed the circuit is primed by connecting the patient venous end 16 to the connector 31 and the patient arterial end 9 to a discharge (for example a collection bag or a discharge connected to the exhausted fluid circuit of the dialysis machine). Then the clamp 32 is opened, the valves 52 and 53 are closed, the pump 8 is activated (with the tract 29 not coupled to the pump 30) in order to aspirate fluid from the port 4 and to circulate the fluid along the venous line 7, the blood filter of the hemodiafilter 5, and the arterial line 6 up to the end 9. The priming of the post-dilution branch 26 is performed by activating the pump 8, closing the venous clamp 18 and opening the valve 53 (with the valve 52 closed), while the priming of the pre-dilution branch 25 is done by opening the valve 52 (with the venous clamp 18 and the valve 53 closed).

In a further embodiment (not shown) the support element comprises a selector configured to selectively squeeze the flexible tube tracts of the pre-dilution and post-dilution branches. The selector comprises a movable (e.g. rotatable) member mounted on (e.g. rotatably coupled to) the support element. The movable member includes a first end and a second end and can assume at least two configurations. In a first configuration the first end squeezes one of the flexible tube tracts and in a second configuration the second end squeezes the other of the flexible tube tracts.

LEGEND

1. Hemo(dia)filtration apparatus
2. Fresh dialyser fluid port
3. Exhausted fluid port 4. On-line port
5. Hemo(dia)filter
6. Arterial line
7. Venous line
8. Blood pump
9. Patient arterial end
10. Pre-pump arterial expansion chamber
11. Blood pump tube tract
12. Post-pump arterial expansion chamber
13. Arterial device end
14. Venous device end
15. Venous expansion chamber
16. Venous patient end
17. Arterial clamp
18. Venous clamp
19. Tubular extensions connected to the chamber 10 for attachment of the blood pump tube tract 11
20. Blood inlet port of the post-pump arterial expansion chamber 12
21. Replacement fluid inlet port of the post-pump arterial expansion chamber 12
22. Outlet port for blood(-replacement fluid) from post-pump arterial expansion chamber 12
23. Replacement fluid supply line
24. Main branch of line 23
25. Pre-dilution branch of line 23
26. Post-dilution branch of line 23
27. Inlet end of line 23
28. Ultrafilter of replacement fluid
29. Replacement fluid pump tube tract
30. Replacement fluid pump
31. Auxiliary connection of line 23 (for priming)
32. Auxiliary connection 31 intercept clamp
33. Intermediate tract of arterial line between the two modules of the hemodiafiltration apparatus
34. Intermediate tract of venous line between the two modules of the hemodiafiltration apparatus
35. Support extensions emerging from the post-pump arterial expansion chamber
36. Casing
37. Mounting extension
38. Tubular extensions for supporting the replacement fluid tube tract
39. First conduit for blood inlet into the post-pump arterial expansion chamber
40. Third blood outlet conduit of the post-pump arterial expansion chamber
41. First flexible tube
42. First tubular connection
43. Second tubular connection
44. Second flexible tube
45. Third flexible tube
46. Seating predisposed on the support element for fixing the main branch 24
47. Expansion reservoir
48. First access of reservoir 47
49. Second access of reservoir 47
50. Second inlet conduit of replacement fluid into the post-pump arterial expansion chamber
51. Diverging tract of the first conduit 39
52. Pre-dilution control valve
53. Post-dilution control valve
54. Connection for service line located at top of expansion reservoir 47
55. Connection for an ultrafilter vent line
56. Connection for the auxiliary line provided with the auxiliary connector 31
57. Connection for an end of the initial tract of replacement fluid line 23 having the inlet 27 at the opposite end
58. Device for detecting pressure in the blood chamber 12
59. Intermediate tract of second conduit 50

The invention claimed is:

1. A hemo(dia)filtration apparatus comprising:
an extracorporeal blood circuit having an arterial line and a venous line;
a supply line of replacement fluid for the extracorporeal blood circuit, said supply line having a bifurcation which divides a main branch into a pre-dilution branch fluidly connected to the arterial line and a post-dilution branch fluidly connected to the venous line;
a pump tube tract predisposed in said supply line for coupling with a pump for circulation of the replacement fluid, said pump tube tract being conformed as an open ring with an aspiration end and a delivery end, the aspiration end having a location, the delivery end having a location;
an expansion chamber having a location and being predisposed in said extracorporeal blood circuit; one of said pre-dilution branch and said post-dilution branch leading to said expansion chamber; the location of the aspiration end and the location of the delivery end being rigidly fixed with respect to the location of the expansion chamber, said expansion chamber bearing said pump tract; and
a support element to which said supply line is constrained such that said pre-dilution branch and said post-dilution branch are located in a pre-determined position with respect to each other and with respect to the location of said expansion chamber, the pre-dilution branch and the post-dilution branch being immobile with respect to said support element, said support element comprising one or more extensions rigidly connected to and integrally formed in a single piece with said expansion chamber, wherein
said pre-dilution branch and said post-dilution branch each comprise at least a squeezable tract of tube, said squeezeble tract of tube being positioned in a pre-fixed postion with respect to the location of said expansion chamber.

2. The apparatus of claim 1, wherein the support element comprises a selector configured to selectively squeeze said squeezable tracts of tube of said pre-dilution and post-dilution branches.

3. The apparatus of claim 1, wherein said squeezable tracts of tube form an angle greater than a right angle.

4. The apparatus of claim 1, wherein said main branch has an end tract terminating at the bifurcation; said end tract of the main branch and a first of said squeezable tracts of tube forming an angle smaller than a right angle.

5. The apparatus of claim 1, wherein a first of said squeezable tracts of tube is oriented obliquely, with reference to an operative configuration in which said pump tube tract is coupled to said pump, and upwardly, with reference to a flow moving from the bifurcation along said first squezzable tract of tube.

6. The apparatus of claim 4, wherein a second of said squeezable tracts of tube forms a prolongation of said end tract of the main branch.

7. The apparatus of claim 1, further comprising a support element, the one of said pre-dilution branch and post-dilution branch not leading to the expansion chamber being constrained directly or via a tract of said extracorporeal blood circuit to the support element.

8. The apparatus of claim 7, wherein said main branch is constrained directly to said support element.

9. The apparatus of claim 8, wherein said main branch comprises an ultrafilter which is directly constrained to said support element.

10. The apparatus of claim 1, wherein said pump tube tract is fluidly arranged in said main branch upstream of said bifurcation.

11. The apparatus of claim 1, wherein said expansion chamber is predisposed in said arterial line and has an inlet fluidly connected to said pre-dilution branch.

12. The apparatus of claim 1, comprising an ultrafilter which is fluidly predisposed in said main branch upstream of said bifurcation, either upstream or downsteam said pump tract.

13. The apparatus of claim 1, comprising a check valve fluidly predisposed in said main branch upstream of said bifurcation.

14. The apparatus of claim 1, comprising a support element mechanically interconnecting said expansion chamber and said supply line and/or said expansion chamber and said extracorporeal blood circuit.

15. The apparatus of claim 14, wherein said expansion chamber is fluidly inserted in said arterial line; the support element mechanically interconnecting said expansion chamber and said venous line or said post-dilution branch.

16. The apparatus of claim 14, wherein said expansion chamber is fluidly inserted in said venous line; the support element mechanically interconnecting said expansion chamber and the arterial line or the pre-dilution branch.

17. The apparatus of claim 14, comprising an ultrafilter which is fluidly predisposed in said main branch upstream of said bifurcation and which is connected in support relationship to said support element.

18. The apparatus of claim 1, wherein the support element comprises an arm which emerges from said expansion chamber and which exhibits at an end thereof a connection with said main branch.

19. The apparatus of claim 1, wherein said supply line comprises at least a system of fluid communication which is fluidly interposed between said delivery end and said expansion chamber and which is provided with one or more of said bifurcation, an ultrafilter, a check valve and a squeezable tube tract.

20. The apparatus of claim 1, wherein said expansion chamber is provided with a pressure monitoring zone for connection to a pressure sensor.

21. The apparatus of claim 1, comprising an integrated element which defines said expansion chamber, a first blood conduit and a second blood conduit; said first and second blood conduits belonging to said extracorporeal blood circuit; said first and second blood conduits each having a lower end which is fluidly connected to said expansion chamber, and an upper end which is fluidly connected to the rest of said extracorporeal blood circuit.

22. The apparatus of claim 21, wherein said first blood conduit is connected to an initial part of said arterial blood line having a patient end which is designed to connect with a vascular access, and wherein said second blood conduit is connected to a final part of said arterial line having a device end designed to connect to a hemo(dia)filter.

23. A hemo(dia)filtration apparatus comprising:
an extracorporeal blood circuit having an arterial line and a venous line;
a supply line of replacement fluid for the extracorporeal blood circuit, said supply line having a bifurcation which divides a main branch into a pre-dilution branch fluidly connected to the arterial line and a post-dilution branch fluidly connected to the venous line;
a pump tube tract predisposed in said supply line for coupling with a pump for circulation of the replacement fluid, said pump tube tract being conformed as an open ring with an aspiration end and a delivery end, the aspiration end having a location, the delivery end having a location;
an expansion chamber having a location and being predisposed in said extracorporeal blood circuit; one of said pre-dilution branch and said post-dilution branch leading to said expansion chamber; the location of the aspiration end and the location of the delivery end being rigidly fixed with respect to the location of the expansion chamber; and
a support element mechanically interconnecting said expansion chamber and said supply line and/or said expansion chamber and said extracorporeal blood circuit, wherein said expansion chamber is fluidly inserted in said arterial line; the support element mechanically interconnecting said expansion chamber and said venous line or said post-dilution branch, wherein the support element comprises one or more extensions rigidly connected to the expansion chamber and a casing engaged to one or more of the extensions.

* * * * *

UNITED STATES PATENT AND TRADEMARK OFFICE
CERTIFICATE OF CORRECTION

PATENT NO. : 8,708,943 B2  
APPLICATION NO. : 12/447796  
DATED : April 29, 2014  
INVENTOR(S) : Caleffi et al.

It is certified that error appears in the above-identified patent and that said Letters Patent is hereby corrected as shown below:

In the Drawings

Figure 5:
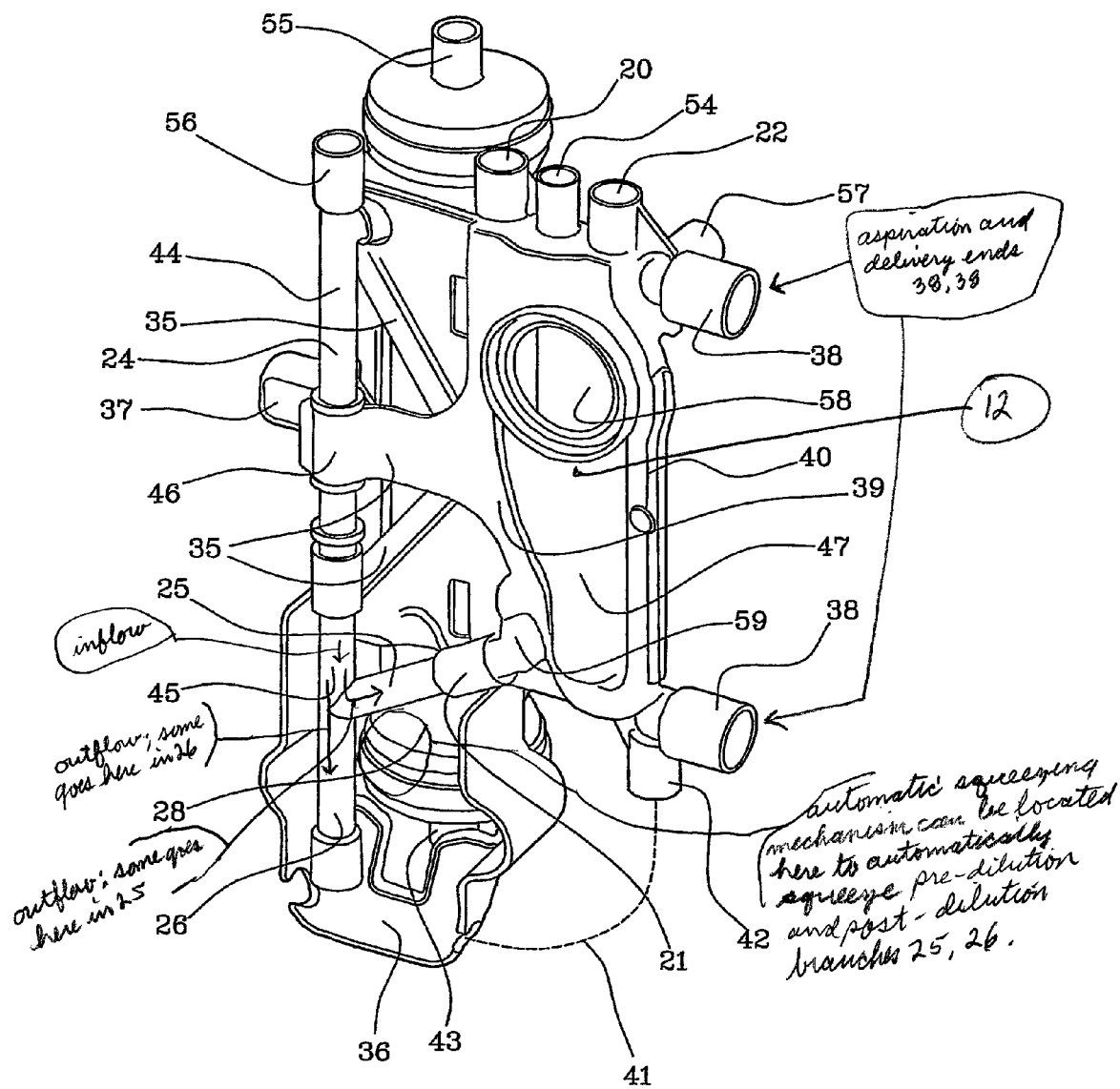
FIG. 5 is a perspective view from behind of the infusion module of the apparatus of FIG. 3, with some parts removed and other parts added with respect to FIG. 3.
Figure 6:
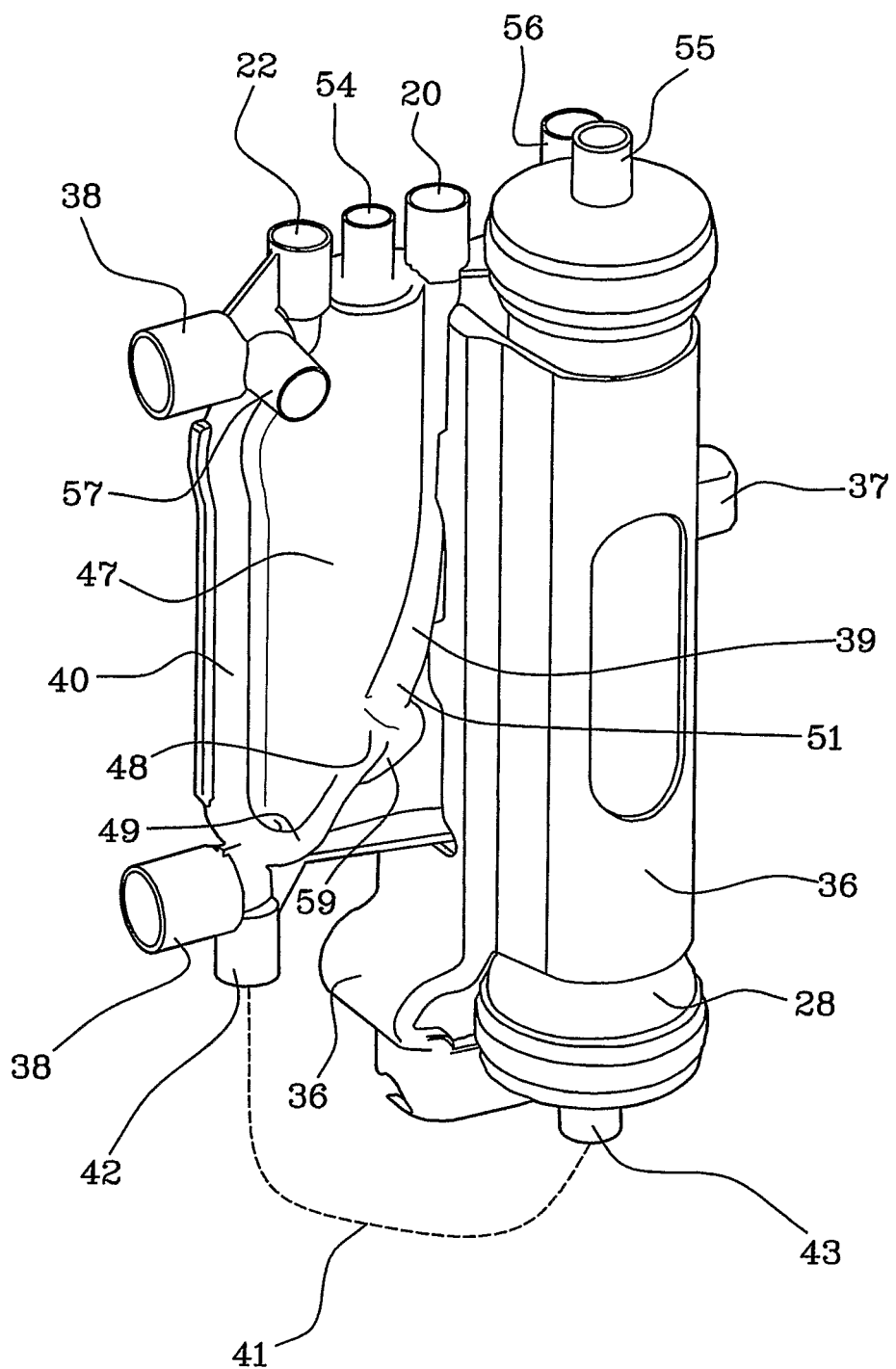
FIG. 6 is a view from the front of FIG. 5.
Figure 7:
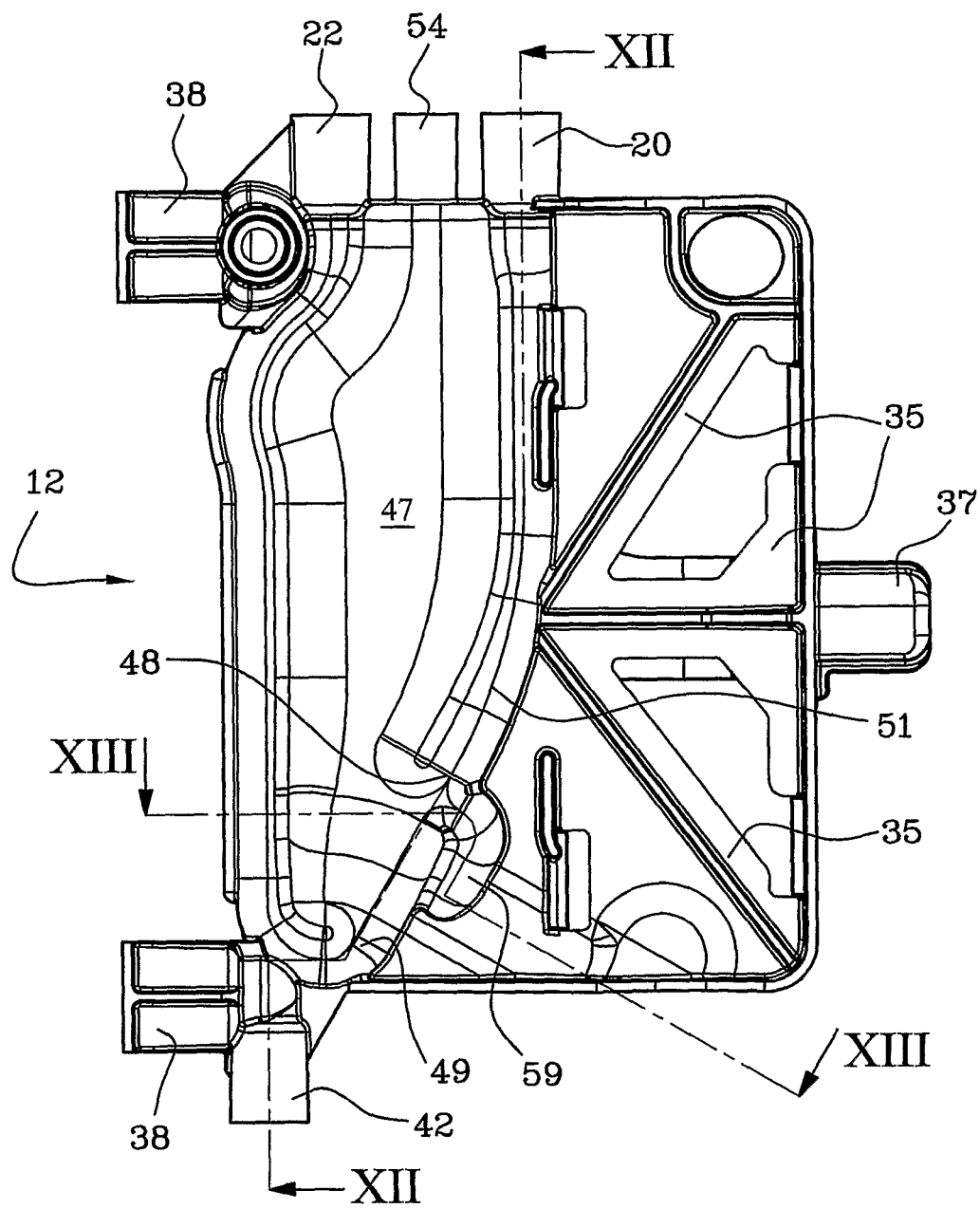
FIG. 7 is a front view of a component of the infusion module of FIG. 3 which includes the blood chamber 12 in which the mixing between the blood and the infused liquid takes place.
Figure 8:
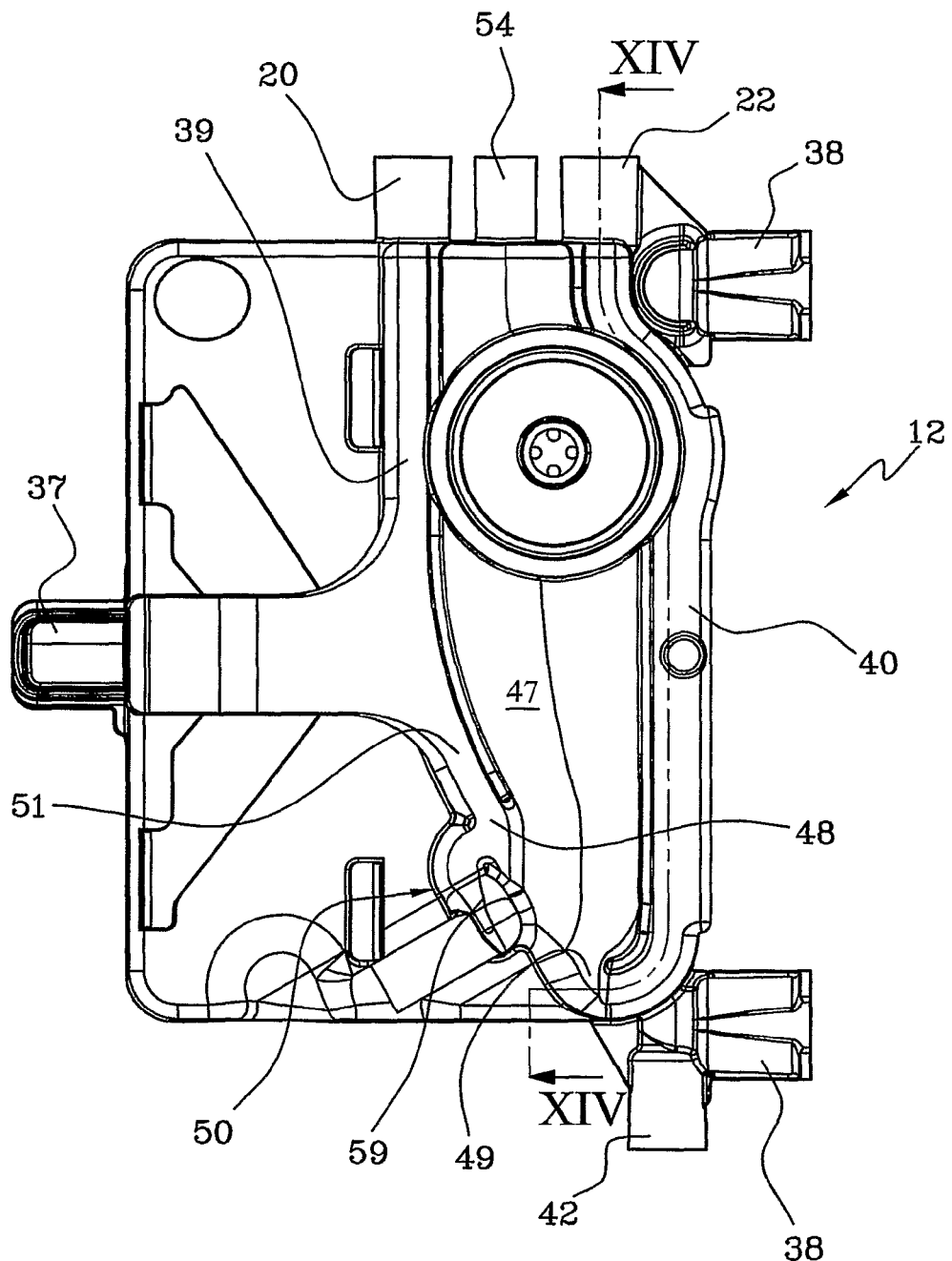
FIG. 8 is a view from behind of FIG. 7.
Figure 10:
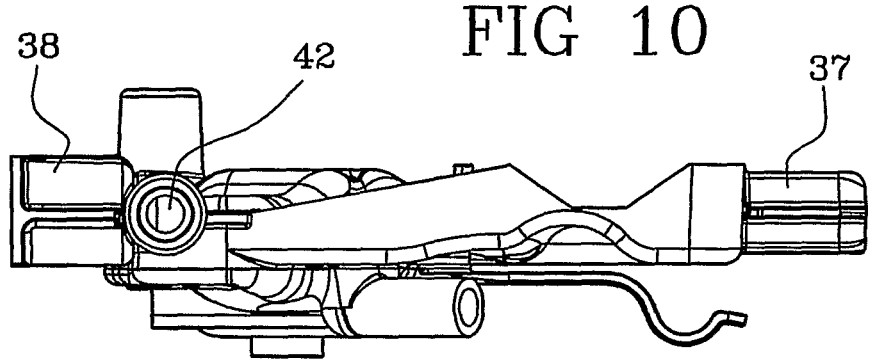
FIG. 10 is a view from below of FIG. 7.
Figure 9:
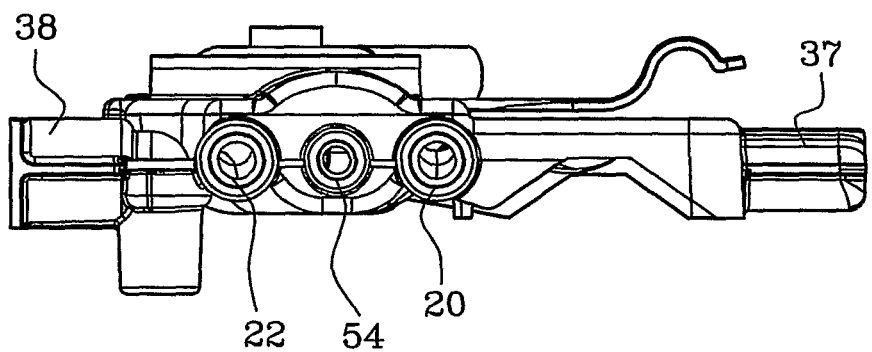
FIG. 9 is a view from above of FIG. 7.
Figures 11, 12:
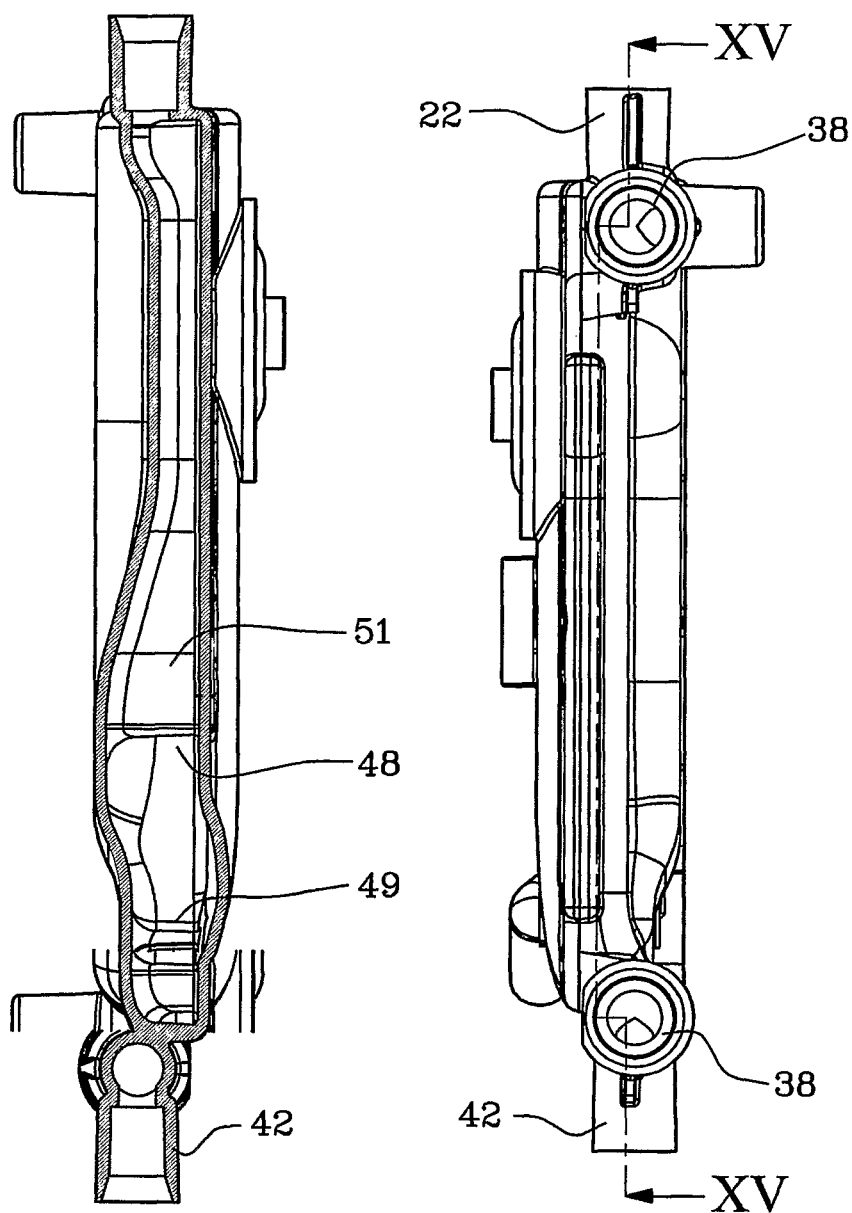
FIG. 11 is a view from the left of FIG. 7.
FIGS. 12, 13, 14 and 15 are sections according respectively to lines XII, XIII, XIV and XV of FIGS. 7, 8 and 11.
Figures 13, 14:
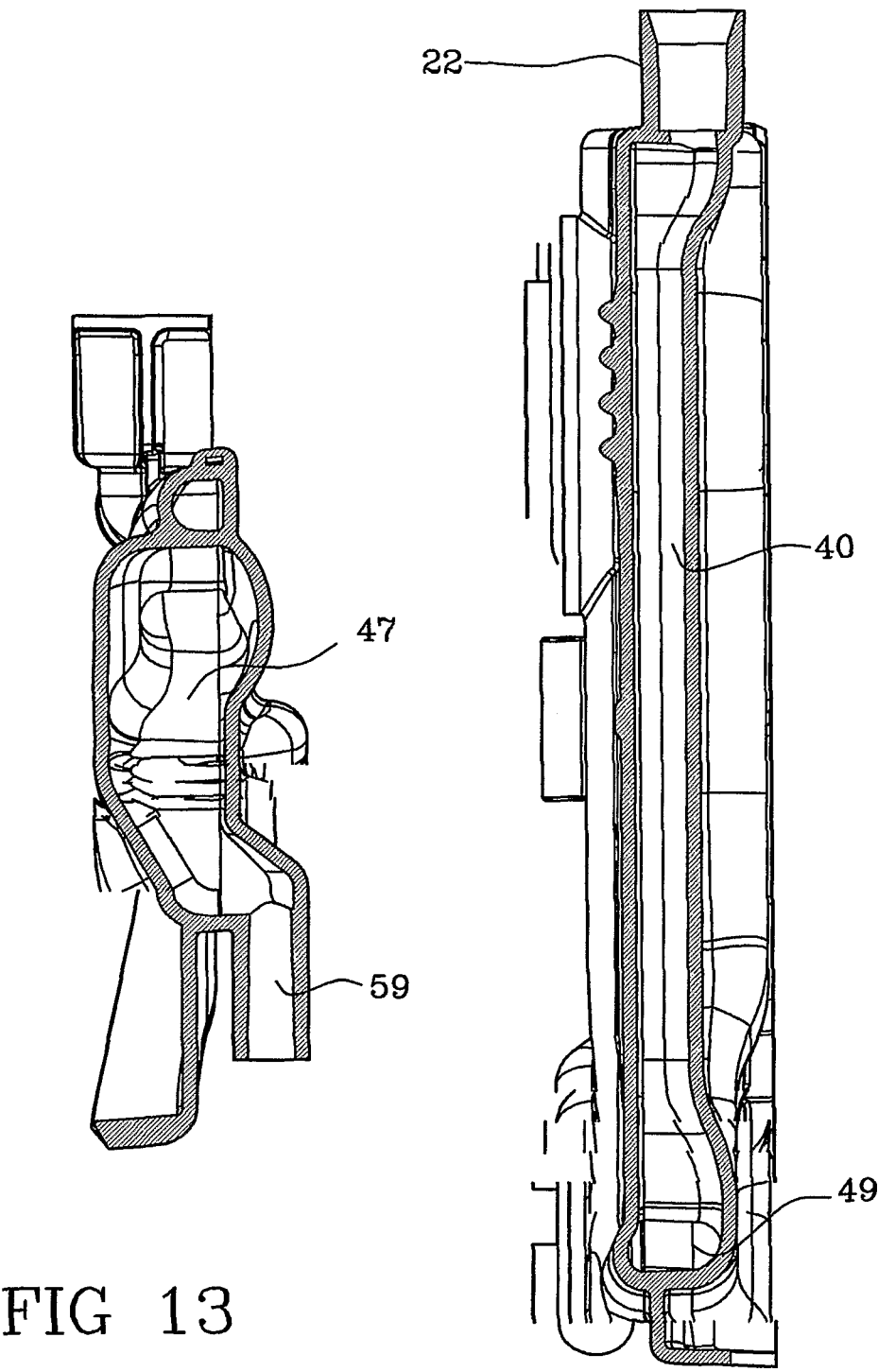
Figure 15:
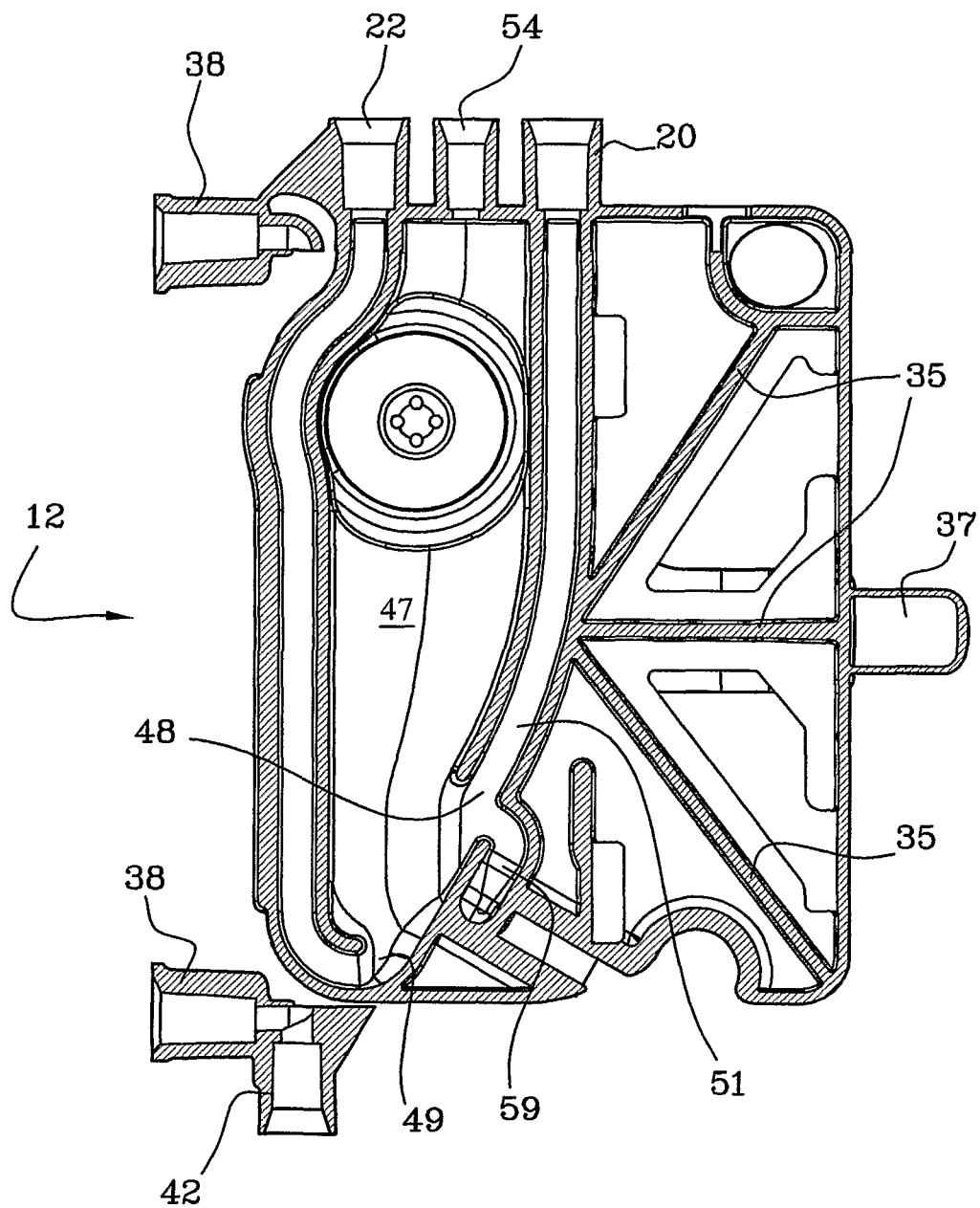

Fig. 5 should be replaced with the corrected Fig. 5 as shown on the attached page.

In the Claim

Column 16 line 40, Claim 1, please delete "zeble tract" and insert therefor --zable tracts--.

Signed and Sealed this
Twenty-third Day of September, 2014

Michelle K. Lee
*Deputy Director of the United States Patent and Trademark Office*

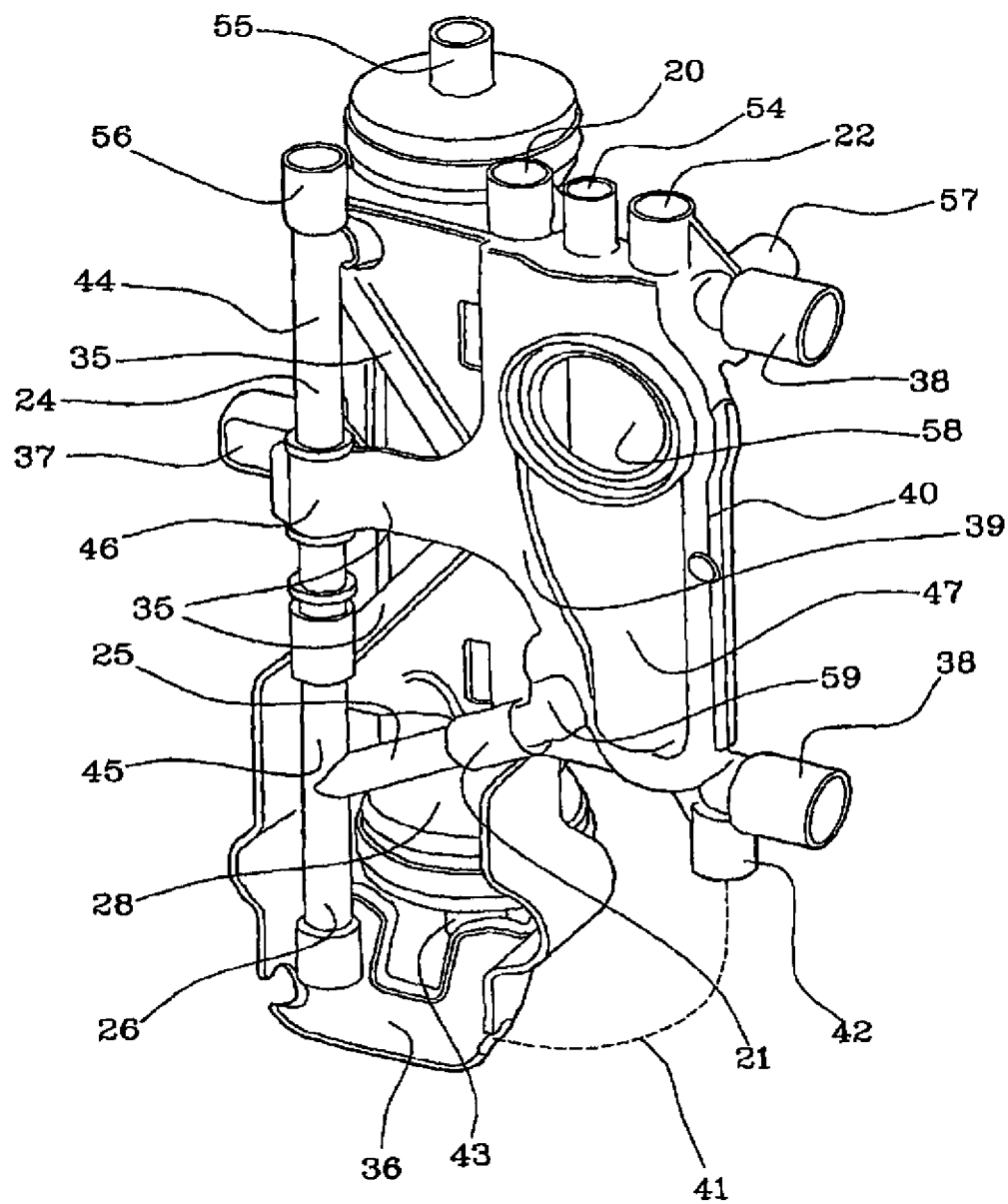

UNITED STATES PATENT AND TRADEMARK OFFICE
CERTIFICATE OF CORRECTION

PATENT NO. : 8,708,943 B2  Page 1 of 1
APPLICATION NO. : 12/447796
DATED : April 29, 2014
INVENTOR(S) : Caleffi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 836 days.

Signed and Sealed this
Twenty-ninth Day of September, 2015

Michelle K. Lee
*Director of the United States Patent and Trademark Office*